United States Patent
Epp et al.

(10) Patent No.: US 7,300,907 B2
(45) Date of Patent: Nov. 27, 2007

(54) 2-(POLY-SUBSTITUTED ARYL)-6-AMINO-5-HALO-4-PYRIMIDINECARBOXYLIC ACIDS AND THEIR USE AS HERBICIDES

(75) Inventors: Jeffrey B. Epp, Noblesville, IN (US); James M. Ruiz, Zionsville, IN (US); Paul R. Schmitzer, Indianapolis, IN (US); Terry W. Balko, Greenfield, IN (US); Thomas L. Siddall, Zionsville, IN (US); Carla N. Yerkes, Crawfordsville, IN (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 11/653,021

(22) Filed: Jan. 12, 2007

(65) Prior Publication Data

US 2007/0179059 A1    Aug. 2, 2007

Related U.S. Application Data

(60) Provisional application No. 60/758,671, filed on Jan. 13, 2006.

(51) Int. Cl.
C07D 239/48 (2006.01)
C07D 239/50 (2006.01)
C07D 401/04 (2006.01)
A01N 43/54 (2006.01)

(52) U.S. Cl. .................. 504/239; 544/326; 544/329

(58) Field of Classification Search ............ 544/326, 544/329; 504/329, 239
See application file for complete search history.

(56) References Cited

FOREIGN PATENT DOCUMENTS

| WO | WO 03/011853 A1 | 2/2003 |
|---|---|---|
| WO | WO2005/063721 A1 | 7/2005 |
| WO | PCT/US2007/000916 | 5/2007 |

OTHER PUBLICATIONS

U.S. Appl. No. 11/653,042, filed Jan. 12, 2007: "6-(Poly-Substituted Aryl)-4-Aminopicolinates and Their use as Herbicides" (claiming priority of U.S. Appl. No. 60/758,701).

*Primary Examiner*—Venkataraman Balasubramanian
(74) *Attorney, Agent, or Firm*—Craig Mixan

(57) ABSTRACT

6-Amino-5-halo-4-pyrimidinecarboxylic acids having poly-substituted aryl substituents in the 2-position, and their amine and acid derivatives, are potent herbicides demonstrating a broad spectrum of weed control.

14 Claims, No Drawings

2-(POLY-SUBSTITUTED ARYL)-6-AMINO-5-HALO-4-PYRIMIDINECARBOXYLIC ACIDS AND THEIR USE AS HERBICIDES

BACKGROUND OF THE INVENTION

This application claims the benefit of U.S. Provisional Application Ser. No. 60/758,671 filed on Jan. 13, 2006.

This invention relates to certain novel 2-(poly-substituted aryl)-6-amino-5-halo-4-pyrimidinecarboxylates and their derivatives and to the use of these compounds as herbicides.

A number of pyrimidinecarboxylic acids and their pesticidal properties have been described in the art. WO 2005/063721 A1 discloses a genus of 2-substituted-6-amino-4-pyrimidinecarboxylic acids and their derivatives and their use as herbicides. It has now been discovered that certain particular subclasses of the genus disclosed in '721 have greatly improved herbicidal activity and selectivity.

SUMMARY OF THE INVENTION

It has now been found that certain 2-(poly-substituted aryl)-6-amino-5-halo-4-pyrimidinecarboxylic acids and their derivatives are superior herbicides with a broad spectrum of weed control against woody plants, grasses and sedges as well as broadleafs and with excellent crop selectivity. The compounds further possess excellent toxicological or environmental profiles.

The invention includes compounds of Formula I:

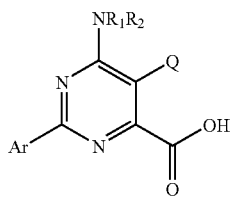

I wherein

Q represents a halogen;

$R_1$ and $R_2$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated ring; and Ar represents a polysubstituted aryl group selected from the group consisting of a)

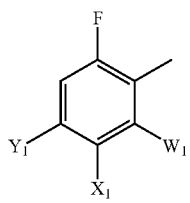

wherein $W_1$ represents F or Cl;

$X_1$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_1$ represents halogen or $C_1$-$C_4$ haloalkyl or, when $X_1$ and $Y_1$ are taken together, represents —$O(CH_2)_nO$— wherein n=1 or 2; and $R_3$ and $R_4$ independently represent H or $C_1$-$C_4$ alkyl;

b)

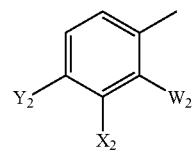

wherein $W_2$ represents F or Cl;

$X_2$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_2$ represents halogen or $C_1$-$C_4$ haloalkyl or, when $X_2$ and $Y_2$ are taken together, represents —$O(CH_2)_nO$— wherein n=1 or 2; and $R_3$ and $R_4$ independently represent H or $C_1$-$C_4$ alkyl; and c)

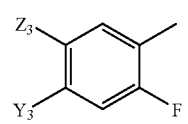

wherein $Y_3$ represents halogen or $C_1$-$C_4$ haloalkyl or, when $Y_3$ and $Z_3$ are taken together, represents —$O(CH_2)_nO$— wherein n=1 or 2;

$Z_3$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$; and $R_3$ and $R_4$ independently represent H or $C_1$-$C_4$ alkyl; and agriculturally acceptable derivatives of the carboxylic acid group.

Compounds of Formula I wherein Q represents Cl and Br, wherein $X_1$ or $X_2$ represent an alkoxy or —$NR_3R_4$, wherein $Y_1$, $Y_2$ or $Y_3$ represent Cl and wherein Ar represents a 2,3,4-trisubstituted phenyl or a 2-fluoro-(4,5,6)-tetrasubstituted phenyl are independently preferred.

The invention includes herbicidal compositions comprising an herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 6-amino-5-halo-4-pyrimidinecarboxylic acids of the formula:

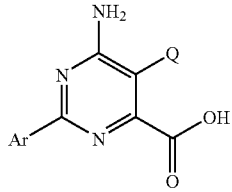

wherein

Q represents a halogen; and

Ar represents a polysubstituted aryl group selected from the group consisting of a)

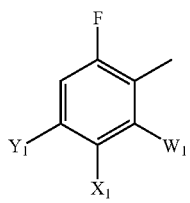

wherein $W_1$ represents F or Cl;

$X_1$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_1$ represents halogen or $C_1$-$C_4$ haloalkyl or, when $X_1$ and $Y_1$ are taken together, represents —$O(CH_2)_nO$— wherein n=1 or 2; and $R_3$ and $R_4$ independently represent H or $C_1$-$C_4$ alkyl;

b)

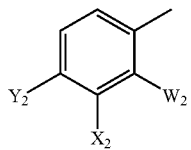

wherein $W_2$ represents F or Cl;

$X_2$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_2$ represents halogen or $C_1$-$C_4$ haloalkyl or, when $X_2$ and $Y_2$ are taken together, represents —$O(CH_2)_nO$— wherein n=1 or 2; and $R_3$ and $R_4$ independently represent H or $C_1$-$C_4$ alkyl; and c)

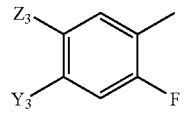

wherein $Y_3$ represents halogen or $C_1$-$C_4$ haloalkyl or, when $Y_3$ and $Z_3$ are taken together, represents —$O(CH_2)_nO$— wherein n=1 or 2;

$Z_3$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$; and $R_3$ and R4 independently represent H or $C_1$-$C_4$ alkyl.

These compounds are characterized by possessing a halogen in the 5-position and a tri- or tetra-substituted aryl group in the 2-position of the pyrimidine ring. Preferred substituted aryl groups include 2,3,4-trisubstituted phenyl and 2-fluoro-(4,5,6)-tetrasubstituted phenyl groups.

The amino group at the 6-position of the pyrimidine ring can be unsubstituted or substituted with one or more $C_1$-$C_6$ alkyl, $C_3$-$C_6$ alkenyl, $C_3$-$C_6$ alkynyl, hydroxy, $C_1$-$C_6$ alkoxy or amino substituents. The amino group can be further derivatized as an amide, a carbamate, a urea, a sulfonamide, a silylamine or a phosphoramidate. Such derivatives are capable of breaking down into the amine. An unsubstituted amino group or one substituted with one or two alkyl substituents is preferred.

The carboxylic acids of Formula I are believed to be the compounds that actually kill or control undesirable vegetation and are typically preferred. Analogs of these compounds in which the acid group of the pyrimidine carboxylic acid is derivatized to form a related substituent that can be transformed within plants or the environment to an acid group possess essentially the same herbicidal effect and are within the scope of the invention. Therefore, an "agriculturally acceptable derivative", when used to describe the carboxylic acid functionality at the 4-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 2-aryl-6-amino-5-halo-4-pyrimidinecarboxylic acid, and (b) is or can be hydrolyzed, oxidized or metabolized in plants or soil to the 4-pyrimidinecarboxylic acid of Formula I that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 6-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 2-aryl-6-amino-5-halo-4-pyrimidinecarboxylic acid, and (b) is or can be hydrolyzed in plants or soil to a free amine of Formula I. N-Oxides which are also capable of breaking into the parent pyrimidine of Formula I are also covered by the scope of this invention.

Suitable salts include those derived from alkali or alkaline earth metals and those derived from ammonia and amines. Preferred cations include sodium, potassium, magnesium, and aminium cations of the formula:

$$R_5R_6R_7NH^+$$

wherein $R_5$, $R_6$, and $R_7$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the 4-pyrimidine carboxylic acids with the alcohol using any number of suitable activating agents such as those used for peptide couplings such as dicyclohexylcarbodiimide (DCC) or carbonyl diimidazole (CDI), by reacting the corresponding acid chloride of a 4-pyrimidinecarboxylic acid of Formula I with an appropriate alcohol, by reacting the corresponding 4-pyrimidinecarboxylic acid of Formula I with an appropriate alcohol in the presence of an acid catalyst or by transesterification. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding 4-pyrimidinecarboxylic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. The terms "alkenyl" and "alkynyl" are intended to include one or more unsaturated bonds.

The term "aryl", as well as derivative terms such as "aryloxy", refers to a phenyl.

Unless specifically limited otherwise, the term "halogen" including derivative terms such as "halo" refers to fluorine, chlorine, bromine, and iodine.

The terms "haloalkyl" and "haloalkoxy" refer to alkyl and alkoxy groups substituted with from 1 to the maximum possible number of halogen atoms.

The compounds of Formula I can be made using well-known chemical procedures. The required starting materials are commercially available or readily synthesized utilizing standard procedures. In the following synthesis schemes, the methyl esters of Formula I are shown as the target compounds and are depicted as Formula IA (see Scheme 1). Compounds of Formula I can be prepared from compounds of Formula IA by the method illustrated in Example 37.

As shown in Scheme 1, the 2-aryl-6-amino-5-halo-4-pyrimidine-carboxylic acid esters of Formula IA can be made from compounds of Formula II by reaction with a halogenating reagent such as N-bromosuccinimide in a solvent such as chloroform or with 1-(chloromethyl)-4-fluoro-1,4-diazoniabicyclo[2,2,2]-octane bis(tetrafluoroborate) (F-TEDA; SELECTFLUOR™ fluorinating agent) in a solvent such as acetonitrile. The method of Scheme 1 is illustrated in Examples 33 and 34.

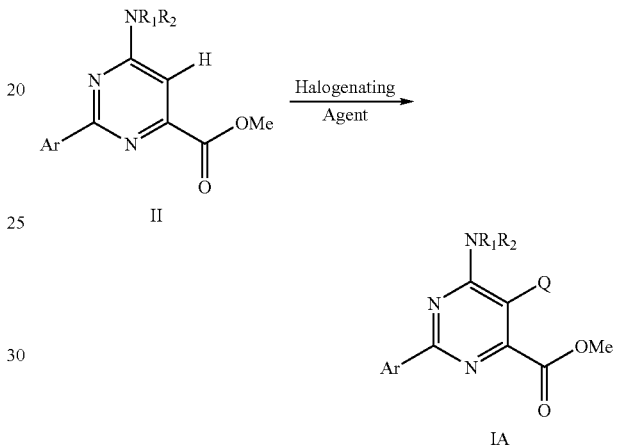

As shown in Scheme 2, the 2-aryl-6-amino-4-pyrimidinecarboxylic acid esters of Formula IA ($Q_1$=halogen) as well as compounds of Formula II ($Q_1$=H) can be prepared by reaction of an appropriately substituted pyrimidine of Formula III with a facile leaving group L, and an organometallic compound of type IV in an inert solvent in the presence of a transition metal catalyst.

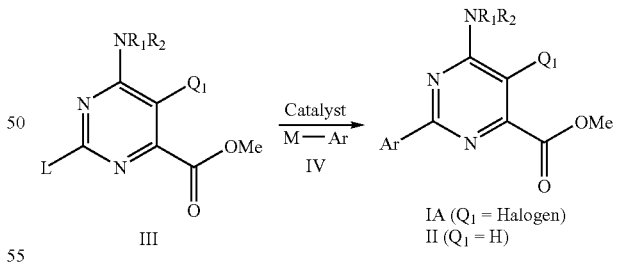

In this case $Q_1$ can be hydrogen or a halogen; L can be chlorine, bromine, iodine or trifluoromethanesulfonate; M can be tri-($C_1$-$C_4$ alkyl)tin or $B(OR_8)(OR_9)$, where $R_8$ and $R_9$ are independently of one another, hydrogen, $C_1$-$C_6$ alkyl, or when taken together form an ethylene or propylene group; and "Catalyst" can be a transition metal catalyst, in particular a palladium catalyst such as bis(triphenylphosphine) palladium(II) dichloride. The method of Scheme 2 is illustrated in Examples 31 and 32.

Alternatively, as shown in Scheme 3, the 2-aryl-6-amino-5-halo-4-pyrimidinecarboxylic acid esters of Formula IA can be prepared from appropriately substituted type V compounds possessing a facile leaving group in the 2-position by reaction with an organometallic compound of type IV in an inert solvent in the presence of a transition metal catalyst; followed by oxidation of the intermediate thioether VI to either sulfoxide or sulfone; followed by reaction with various amines (VII). In this case, Q is a halogen; $R_{10}$ can be an alkyl or aryl group; L can be chlorine, bromine, iodo or trifluoromethanesulfonate; M can be tri-($C_1$-$C_4$ alkyl)tin or B($OR_8$)($OR_9$), where $R_8$ and $R_9$ are independently of one another, hydrogen, $C_1$-$C_6$ alkyl, or when taken together form an ethylene or propylene group; and "Catalyst" can be a transition metal catalyst, in particular a palladium catalyst such as bis(triphenylphosphine)palladium(II) dichloride. The method of Scheme 3 is illustrated in Examples 27 and 28.

Scheme 3

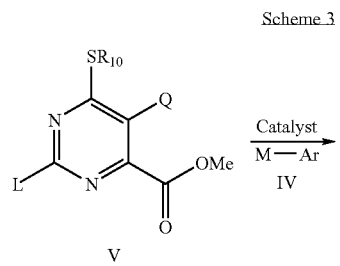

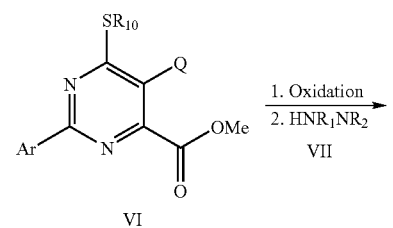

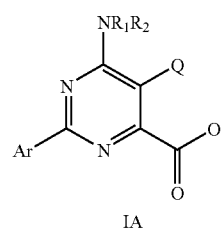

Alternatively, as shown in Scheme 4, the 2-aryl-6-amino-5-halo-4-pyrimidinecarboxylic acid esters of Formula IA can be prepared from appropriately substituted type VIII compounds substituted with a metal in the Scheme 4

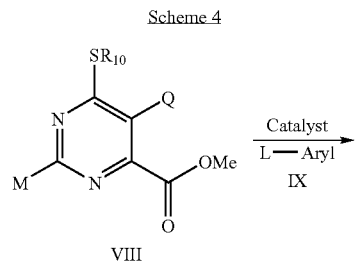

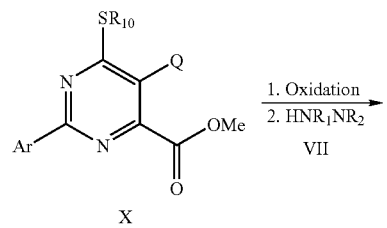

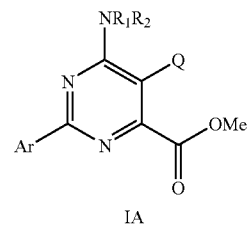

2-position by reaction with an aryl compound of type IX in an inert solvent in the presence of a transition metal catalyst; followed by oxidation of the intermediate thioether X to either sulfoxide or sulfone; followed by reaction with various amines (VII). In this case, Q is a halogen; $R_{10}$ can be an alkyl or aryl group; L can be chlorine, bromine, iodine or trifluoromethanesulfonate; M can be tri-($C_1$-$C_4$ alkyl)tin; and "Catalyst" can be a transition metal catalyst, in particular a palladium catalyst such bis(triphenylphosphine)palladium(II)dichloride. The method of Scheme 4 is illustrated in Examples 29 and 30.

The coupling of III+IV, V+IV, and VIII+IX may, where appropriate, be followed by reactions on either ring to obtain further derivatives of the compounds of Formula IA.

As shown in Scheme 5, appropriately substituted pyrimidines of Formula m where $Q_1$ is a halogen and L is chloro or bromo can be obtained by reaction of pyrimidine XI ($Q_1$ is a halogen and L is chloro or bromo) with amines of type VII. Also shown in Scheme 5, appropriately substituted pyrimidines of Formula V where $Q_1$ is halogen; $R_{10}$ is an alkyl or aryl group; and L is chloro or bromo can be easily obtained by reaction of pyrimidine XI ($Q_1$ is halogen and L is chloro or bromo) with thiolate salts of type XII in solvent system consisting of a mixture of benzene and water.

Scheme 5

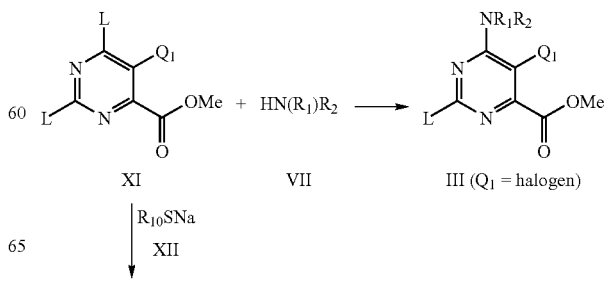

-continued

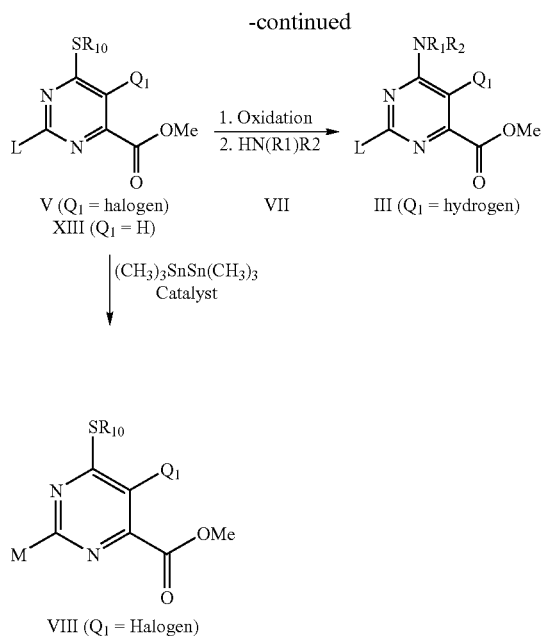

V (Q₁ = halogen)
XIII (Q₁ = H)

VII

III (Q₁ = hydrogen)

VIII (Q₁ = Halogen)

Also shown in Scheme 5, appropriately substituted pyrimidines of Formula III where $Q_1$ is a hydrogen and L is chloro or bromo can be prepared by reaction of pyrimidines of Formula XI ($Q_1$ is a hydrogen and L is chloro or bromo) with thiolate salts of type XII in a solvent system consisting of a mixture of benzene and water; followed by oxidation of the intermediate thioether XIII; followed by reaction with amines of type VII.

Finally shown in Scheme 5, appropriately substituted pyrimidines of Formula VIII where $Q_1$ is a halogen; $R_{10}$ is an alkyl or aryl group; and M is trimethyltin can be made by reaction of V ($Q_1$ is a halogen and L is chloro or bromo) with hexamethylditin in an inert solvent such as dioxane in the presence of a transition metal catalyst such as bis(triphenylphosphine)palladium(II) dichloride. The methods of Scheme 5 are illustrated in Examples 21-26.

As shown in Scheme 6, appropriately substituted pyrimidines of Formula XI where $Q_1$ is hydrogen or halogen and L is chloro or bromo can be prepared from compounds of Formula XIV ($Q_1$ is hydrogen or chloro, see H. Gershon, *J. Org. Chem.* 1962, 27, 3507-3510 for preparation) by reaction with reagents such as phosphorous oxychloride or phosphorous oxybromide. The reaction can be run neat or in the presence of a solvent such as sulfolane. The method of Scheme 6 is illustrated in Example 20.

Scheme 6

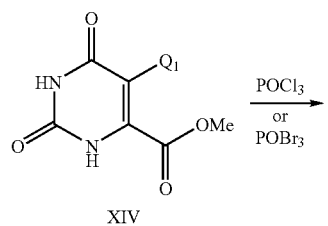

XIV

-continued

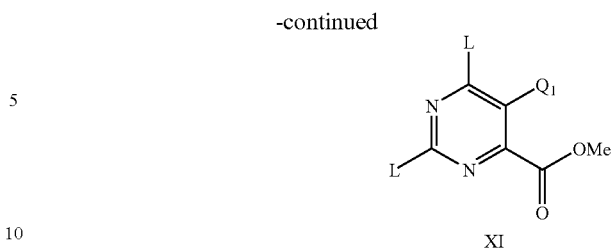

XI

For other methods to prepare compounds of Formula I, see WO 2005/063721 A1.

It is recognized that some reagents and reaction conditions described above for preparing compounds of Formula I may not be compatible with certain functionalitites present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may necessary to perform a combination of the steps illustrated in the above schemes in an order other than that implied by the particular sequence presented to prepare the compounds of Formula I.

Finally, one skilled in the art will also recognize that compounds of Formula I and the intermediates described herein can be subjected to various electrophilic, nucleophilic, radical, organometallic, oxidation, and reduction reactions to add substituents or modify existing substituents.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds postemergence. It is further usually preferred to use the compounds to control a wide spectrum of woody plants, broadleaf and grass weeds, and sedges. Use of the compounds to control undesirable vegetation in established crops is especially indicated. While each of the 2-aryl-6-amino-5-halo-4-pyrimidinecarboxylate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 1,000 g/Ha are generally employed in postemergence operations; for preemergence applications, rates of about 10 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compounds of the present invention can, further, be used in conjunction with glyphosate, glufosinate or 2,4-D on glyphosate-tolerant, glufosinate-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 2-aryl-6-amino-5-halo-4-pyrimidinecarboxylate compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

1. Preparation of 3-bromo-6-chloro-2-fluorophenol

A solution of 1-bromo-4-chloro-2-fluorobenzene (20.4 g, 0.100 mol) in tetrahydrofuran (THF; 50 mL) was slowly added to lithium diisopropylamide (LDA; 0.125 mol) in THF (600 mL) at −50° C. After addition, the solution was warmed to −20° C. and then cooled to −50° C. A solution of trimethyl borate (13.5 g, 0.130 mol) in THF (20 mL) was added slowly and the temperature was warmed to −20° C. The mixture was then cooled to −70° C. and a solution of peracetic acid (32% in acetic acid, 0.150 mol) was slowly added and the mixture was warmed to ambient temperature. Water (250 mL) was added and the solution was extracted with ethyl acetate (2×200 mL). The combined organic phases were dried and concentrated. The black oil was purified by column chromatography (20% ethyl acetate in hexanes) to give 3-bromo-6-chloro-2-fluorophenol (14.1 g, 0.063 mol) $^1$H NMR (CDCl$_3$): δ 7.05 (m, 2H), 5.5 (br s, 1H).

Another phenol prepared according to the procedure of Example 1 was:

3-Bromo-2,6-dichlorophenol: mp 69-70° C.

2. Preparation of 1-bromo-4-chloro-2-fluoro-3-methoxybenzene

A heterogeneous mixture of 3-bromo-6-chloro-2-fluorophenol (14.4 g, 0.064 mol), methyl iodide (13.5 g, 0.096 mol) and potassium carbonate (8.8 g, 0.064 mol) in acetonitrile (100 mL) was heated under reflux for two hours. The mixture was cooled, diluted with water (100 mL) and extracted with diethyl ether (2×150 mL). The combined extracts were dried and concentrated. The dark oil was purified by chromatography (5% ethyl acetate in hexanes) to give 1-bromo-4-chloro-2-fluoro-3-methoxybenzene (14.8 g, 0.062 mol) $^1$H NMR (CDCl$_3$): δ 7.20 (m, 1H), 7.10 (dd, 1 H), 4.0 (s, 3H).

Other compounds prepared according to the procedure of Example 2 include:

1-Bromo-4-chloro-3-ethoxy-2-fluorobenzene: $^1$H NMR (CDCl$_3$) δ 7.20 (m, 1H), 7.10 (dd, 1H), 4.20 (q, 2H), 1.50 (t, 3H). 1-Bromo-2,4-dichloro-3-methoxybenzene: $^1$H NMR (CDCl$_3$) δ 7.35 (d, 1H), 7.15 (d, 1H), 3.95 (s, 3H). 1-Chloro-3,5-difluoro-2-methoxybenzene: GC-MS (m/z=178).

3. Preparation of 1-bromo-4-chloro-2-fluoro-5-methoxybenzene

A solution of 4-chloro-2-fluoro-5-methoxyaniline (25.0 g, 0.143 mol) in 10% HBr (250 mL) was cooled to 0° C. and a solution of sodium nitrite (15.0 g, 0.218 mol) in water (20 mL) was slowly added. After addition, methylene chloride (50 mL) and cupric bromide (30.0 g, 0.244 mol) were added slowly. The reaction mixture was then warmed to ambient temperature, stirred for one hour, filtered through a bed of celite, and extracted with methylene chloride (2×100 mL). The combined organic phases were dried and concentrated. Chromatography of the dark oil (5% ethyl acetate in hexanes) gave 1-bromo-4-chloro-2-fluoro-5-methoxybenzene (16.6 g, 0.070 mol): $^1$H NMR (CDCl$_3$): δ 7.20 (m, 1H), 7.05 (dd, 1H), 4.00 (s, 3H).

4. Preparation of 1-chloro-3,5-difluoro-4-iodo-2-methoxybenzene

2-Chloro-4,6-difluoroanisole (2.0 g, 11 mmol) was dissolved in 20 mL anhydrous THF and cooled to −70 to −75° C. 2.5M n-Butyl lithium in hexanes (6.7 mL, 17 mmol) was added dropwise. After stirring for 75 minutes at −75° C., the mixture was treated dropwise with a solution of iodine (5.1 g, 20 mmol) in 10 mL THF. After stirring for 20 minutes, the reaction solution was allowed to warm to 25° C. over 40 minutes. The reaction mixture was diluted with Et$_2$O (50 mL) and stirred with dilute NaHSO$_3$ solution to destroy excess iodine. The separated aqueous phase was extracted with 20 mL Et$_2$O. The combined ether phases were washed with saturated NaCl, dried, and evaporated to give 1-chloro-3,5-difluoro-4-iodo-2-methoxybenzene (3.1 g, 91% yield): mp 62-64° C.; GC-MS (m/z=304).

5. Preparation of 1-bromo-4-chloro-3-(2,2-difluoroethoxy)-2-fluorobenzene

A solution of 3-bromo-6-chloro-2-fluorophenol (15.4 g, 0.068 mol) in dimethylformamide (DMF; 25 mL) was slowly added to a suspension of sodium hydride (60% dispersion in mineral oil) (4.0 g, 0.10 mol) in DMF (100 mL) and the reaction mixture was stirred one hour. A solution of methanesulfonic acid 2,2-difluoroethyl ester (17.5 g, 0.109 mol) in DMF (10 mL) was slowly added. The resulting solution was heated at 70° C. for eighteen hours. The cooled solution was diluted with water (200 mL) and extracted with ethyl ether. The combined organic phases were dried and concentrated. The residual oil was purified by column chromatography (in hexanes) to give 1-bromo-4-chloro-3-(2,2-difluoroethoxy)-2-fluorobenzene (9.0 g, 0.031 mol): $^1$H NMR (CDCl$_3$): δ 7.26 (m, 1H), 7.09 (m, 1H), 6.12 (tt, 1H), 4.30 (td, 2H).

6. Preparation of 1-bromo-4-chloro-3-methylthio-2-fluorobenzene

A solution of 1-bromo-4-chloro-2-fluorobenzene (20.4 g, 0.100 mol) in THF (50 mL) was slowly added to LDA (0.125 mol) in THF (600 mL) at −50° C. After addition, the solution was warmed to −20° C. and then cooled to −50° C. A solution of dimethyldisulfide (18.8 g, 0.20 mol) in THF (50 mL) was then slowly added and the mixture was warmed to ambient temperature. The reaction was quenched with water (200 mL), extracted with ethyl acetate (2×150 mL), and the combined organic phases dried and concentrated. The residual red oil was purified by chromatography (5% ethyl acetate in hexanes) to give 1-bromo-4-chloro-3-methylthio-2-fluorobenzene (23.9 g, 0.094 mol): $^1$H NMR (CDCl$_3$): δ 7.40 (m, 1H), 7.15 (dd, 1H), 2.50 (s, 3H).

7. Preparation of 1-bromo-4-chloro-2-fluoro-3-methylbenzene

Diisopropylamine (15.2 g, 150 mmol) was dissolved in 100 mL THF and the solution was cooled to −50° C. 2.5M n-butyl lithium (50 mL, 125 mmol) was added dropwise by addition funnel and the solution was again cooled to −50° C. 1-Bromo-4-chloro-2-fluorobenzene (20.95 g, 100 mmol) in 25 mL THF was then slowly added to the LDA solution at −50° C. keeping the temperature below −25° C., after which the solution was allowed to warm to −15° C. The reaction mixture was then cooled again to −60° C. and iodomethane (9.33 mL, 150 mmol) was added dropwise. The resulting solution was allowed to warm to room temperature and concentrated under vacuum. The residue was partitioned between ethyl acetate and water. The organic phase was washed with water, dried, and concentrated under vacuum. The product was purified by column chromatography using hexanes as the sole solvent to yield 1-bromo-4-chloro-2-fluoro-3-methylbenzene (19.3 g, 86% yield): $^1$H NMR (CDCl$_3$): δ 7.30 (m, 1H), 7.05 (dd, 1H), 2.35 (d, 3H).

8. Preparation of 3-bromo-6-chloro-2-fluorobenzaldehyde

A solution of 1-bromo-4-chloro-2-fluorobenzene (20.4 g, 0.100 mol) in THF (50 mL) was slowly added to LDA (0.125 mol) in THF (600 mL) at −50° C. The resulting solution was then warmed to −20° C. and cooled again to −50° C. A solution of DMF (14.6 g, 0.20 mol) in THF (50 mL) was slowly added and the reaction mixture was allowed to warm to room temperature. The reaction was quenched with water (250 mL) and extracted with ethyl acetate (2×150 mL). The combined organic phases were dried and concentrated. The product was recrystallized from hexane to give 3-bromo-6-chloro-2-fluorobenzaldehyde (40.0 g, 0.169 mol): mp 92–93° C.

9. Preparation of 1-bromo-4-chloro-2-fluoro-3-difluoromethylbenzene

Diethylamino sulfur trifluoride (15.3 g, 0.096 mol) was added slowly to a solution of 3-bromo-6-chloro-2-fluorobenzaldehyde (7.50 g, 0.032 mol) in methylene chloride at 0° C. The resulting solution was stirred for one hour and then allowed to warm to room temperature. The reaction was carefully quenched with a saturated solution of sodium bicarbonate in water (100 mL) and extracted with methylene chloride (2×75 mL). The combined organic extracts were dried and concentrated to give 1-bromo-4-chloro-2-fluoro-3-difluoro-methylbenzene (7.20 g, 0.028 mol): $^1$H NMR (CDCl$_3$): δ 7.60 (m, 1H), 7.05 (m, 1H), 7.00 (d, 1H).

10. Preparation of 2,4-dichloro-3-methoxyphenylboronic acid

To a solution of 1-bromo-2,4-dichloro-3-methoxybenzene (5.12 g, 20 mmol) in diethyl ether cooled to −70° C. was added 2.5M n-butyl lithium (8.8 mL, 22 mmol) in portions keeping the temperature below −60° C. The resulting reaction mixture was then stirred for 10 minutes before triisopropylborate (6.9 mL, 30 mmol) was added in portions keeping the temperature below −60° C. The reaction mixture was then allowed to warm to room temperature and acetyl chloride (60 mmol) was added. The reaction mixture was stirred for an hour at room temperature and concentrated. The residue was partitioned between ethyl acetate and 1N NaOH (40 mL) and the organic phase was extracted with additional 1N NaOH (10 mL). The sodium hydroxide extracts were combined, ice was added, and the solution was acidified to pH 3-4 with concentrated HCl. The product was then extracted with ethyl acetate and the organic phase was dried and concentrated to yield 2,4-dichloro-3-methoxyphenylboronic acid (3.27 g, 14.8 mmol): $^1$H NMR (CDCl$_3$): δ 8.44 (br s, 2H), 7.42 (d, 1H), 7.15 (d, 1H), 3.8 (s, 3H).

Other boronic acids prepared according to the procedure of Example 10 include:

4-Chloro-2-fluoro-3-methylthiophenylboronic acid: $^1$H NMR (CDCl$_3$): δ 8.39 (br s, 2H), 7.49 (m, 1H), 7.35 (m, 1H), 2.43 (s, 3H). 4-Chloro-2-fluoro-3-methylphenylboronic acid:$^1$H NMR (DMSO-d$_6$): δ 8.27 (br s, 2H), 7.5–7.2 (m, 2H), 2.25 (m, 3H). 4-Chloro-3-(2,2-difluoroethoxy)-2-fluorophenylboronic acid:$^1$H NMR (DMSO-d$_6$): δ 8.38 (br s, 2H), 7.52 (m, 1H), 7.29 (M, 1H), 6.33 (tt, 1H), 4.32 (m, 2H).

11. Preparation of 2-(4-chloro-2-fluoro-3-methoxyphenyl)-[1,3,2]-dioxaborinane To a solution of 1-bromo-4-chloro-2-fluoro-3-methoxybenzene (10.4 g, 0.043 mol) in diethyl ether (150 mL) at −78° C. was slowly added n-butyl lithium (2.5M, 19.0 mL, 0.0475 mol), and the solution was stirred for thirty minutes. A solution of triisopropyl borate (12.0 g, 0.064 mL) in THF (25 mL) was slowly added and the solution warmed to 0° C. Acetyl chloride (10.0 g, 0.13 mol) was added. After stirring for one hour the solution was concentrated and the solid residue was partitioned between ethyl acetate (150 mL) and 1N sodium hydroxide (50 mL). Ice was added to the aqueous phase that was subsequently acidified with sufficient concentrated hydrochloric acid to obtain a pH of 2. The heterogeneous mixture was extracted with ethyl acetate (2×150 mL) and the combined organic phases were dried and concentrated. The resulting solid was slurried in toluene, propane-1,3-diol (6.6 g, 0.09 mol) was added, and the resulting mixture was heated under reflux to remove water via a Dean-Stark trap. After two hours, the mixture was allowed to cool and was concentrated under vacuum. The resulting oil was dissolved in methylene chloride (50 mL), washed with water (25 mL), dried, and concentrated to give 2-(4-chloro-2-fluoro-3-methoxyphenyl)-[1,3,2]-dioxaborinane (6.4 g, 0.062 mol): $^1$H NMR (CDCl$_3$): δ 7.15 (m, 1H), 6.95 (dd, 1H), 4.05 (t, 4H), 3.8 (s, 3H), 1.95 (t, 2H).

Other compounds prepared according to the procedure of Example 11 include:

2-(4-Chloro-2-fluoro-5-methoxyphenyl)-[1,3,2]-dioxaborinane: $^1$H NMR (CDCl$_3$): δ 7.25 (d, 1H), 7.05 (d, 1H), 4.20 (t, 4H), 4.15 (s, 3H), 2.10 (t, 2H). 2-(4-Chloro-2-fluoro-3-difluoromethylphenyl)-[1,3,2]-dioxaborinane $^1$H NMR (CDCl$_3$): δ7.75 (m, 1H), 7.15 (dd, 1H), 6.90-7.15 (t, 1H) 4.20 (t, 4H), 2.05 (t, 2H).

12. Preparation of (4-chloro-3-ethoxy-2-fluorophenyl)trimethylstannane

1-Bromo-4-chloro-3-ethoxy-2-fluorobenzene: (3.55 g, 14 mmol) and hexamethylditin (5.9 g, 18 mmol) were dissolved in 25 mL p-dioxane and bis(triphenylphosphine)palladium (II) dichloride (491 mg, 0.70 mmol) was added. The reaction mixture was heated at 100° C. for 5 hours, allowed to cool to room temperature and concentrated. The residue was purified by column chromatography (0-5% ethyl acetate/hexane gradient) to yield (4-chloro-3-ethoxy-2-fluorophenyl)trimethylstannane (4.3 g, 12.7 mmol); 85% pure by GC-MS m/z 338 (M$^+$).

13. Preparation of 1-fluoro-2,3-methylenedioxybenzene

Alliquat 336 (methyltrioctylammonium chloride (0.63 g, 0.0016 mol), dibromomethane (40.7 g, 234.2 mmol), and water (31 mL) were placed in a 500 mL 3-necked flask equipped with an addition funnel, condenser and a stir bar. The addition funnel was charged with a solution of 3-fluorocatechol (20.0 g, 6.1 mmol) in 5M sodium hydroxide (80 mL). The mixture in the flask was heated to reflux and the solution of the catechol was added dropwise with good stirring over 1.5 hours. The resulting dark mixture was heated an additional 2 hours at reflux. After cooling to room temperature, the reaction was diluted with methylene chloride and water. The aqueous layer was extracted with methylene chloride and the combined organic layers were dried and concentrated to give 1-fluoro-2,3-methylenedioxybenzene (14.6 g, 104.2 mmol) as a dark yellow oil: $^1$H NMR (CDCl$_3$): δ 6.80 (m, 1H), 6.68 (m, 2H), 6.04 (s, 2H).

14. Preparation of 2-fluoro-3,4-methylenedioxyphenylboronic acid

1-Fluoro-2,3-methylenedioxybenzene (5.0 g, 35.7 mmol) was dissolved in THF (70 mL) and the solution was cooled to −65° C. in a dry ice acetone bath. n-Butyl lithium (2.5 g, 15.7 mL, 39.3 mmol) was added to the solution via syringe with stirring. The reaction was allowed to warm to −35° C. over 1 hour, then cooled to −65° C. and treated with trimethylborate (4.1 g, 39.3 mmol) via syringe. The reaction was allowed to warm slowly to room temperature, quenched with 1N HCl (50 mL), stirred for 15 minutes, and then extracted with ether. The organic phase was then extracted with 1N sodium hydroxide and this aqueous extract was then acidified with 1N hydrochloric acid. The acidic aqueous solution was then extracted with two portions of ether and these combined ether extracts were dried and concentrated to an oily solid that was triturated with methylene chloride. The resulting solid was collected by filtration, washed with methylene chloride, and dried to give 1-fluoro-2,3-methylenedioxyphenylboronic acid (1.4 g, 7.6 mmol) as a tan solid: $^1$H NMR (DMSO-d$_6$): δ 8.05 (br s, 2H), 7.08 (dd, 1H, J=7.8, 5.1 Hz), 6.76 (d, 1H, J=7.8 Hz), 6.08 (s, 2H).

15. Preparation of 3-bromo-6-chloro-2-fluorobenzonitrile

A suspension of 3-bromo-6-chloro-2-fluorobenzaldehyde (9.0 g, 0.04 mol) and hydroxylamine-O-sulfonic acid (7.50 g, 0.07 mole) in water (300 mL) was heated at 50° C. for eighteen hours. The suspension was cooled and the solid was collected to give 3-bromo-6-chloro-2-fluorobenzonitrile (8.8 g, 0.04 mol): $^1$H NMR (CDCl$_3$): δ 7.75 (m, 1H), 7.25 (m, 1H).

16. Preparation of 3-bromo-2-fluoro-6-chlorobenzamide

Concentrated sulfuric acid (15 mL) was placed in a 100 mL 3-neck flask equipped with an internal thermometer and heated to 55° C. 3-Bromo-2-fluoro-6-chlorobenzonitrile (11.0 g, 47 mmol) was added portion-wise to the acid with stirring maintaining the temperature above 50° C. The dark solution was heated at 65° C. for 24 hours, allowed to cool to room temperature, poured over ice, and cautiously neutralized with concentrated ammonium hydroxide. The mixture was extracted with two portions of ethyl acetate and the combined organic layers were dried and concentrated to give 3-bromo-2-fluoro-6-chlorobenzamide (11.5 g, 45.5 mmol) as a light orange solid: mp 157-158° C., $^1$H NMR (CDCl$_3$): δ 7.54 (t, 1H), 7.14 (dd, 1H), 6.03 (br s, 1H) 5.81 (br s, 1H).

17. Preparation of 3-bromo-6-chloro-2-fluoroaniline

Sodium hydroxide (4 g, 100.0 mmol) was dissolved in water (70 mL) and the resulting solution was cooled in an ice bath and treated with bromine (4.7 g, 29.7 mmol). Solid 3-bromo-2-fluoro-6-chlorobenzenecarboxamide (5.0 g, 19.9 mmol) was added slowly with good stirring and the orange mixture was heated to reflux for 2 hours. The cooled reaction mixture was extracted with methylene chloride and the organic phase was dried and concentrated. Recrystallization of the product from cold hexanes gave 3-bromo-6-chloro-2-fluoroaniline (2.8 g, 12.6 mmol) as an off white solid: mp 61-62° C.: $^1$H NMR (CDCl$_3$): δ 6.94 (dd, 1H), 6.83 (dd, 1H), 4.16 (br s, 2H).

18. Preparation of N-(3-bromo-6-chloro-2-fluorophenyl)-N,N-dimethylamine

3-Bromo-6-chloro-2-fluoroaniline (2.5 g, 11.1 mmol) was dissolved in THF (25 mL) and treated with 37% formaldehyde (0.84 g, 2.1 mL, 27.8 mmol), dibutyltindichloride (0.07 g, 0.22 mmol), and phenyl silane (1.33 g, 12.3 mmol). The resulting solution was then stirred at room temperature under nitrogen for 48 hours. The reaction mixture was concentrated under vacuum and purified by column chromatography (hexanes) to give N-(3-bromo-6-chloro-2-fluorophenyl)-N,N-dimethylamine (2.0 g, 7.9 mmol) as an oil: $^1$H NMR (CDCl$_3$): δ 7.19 (dd, 1H), 7.04 (dd, 1H), 2.88 (s, 3H), 2.87 (s, 3H).

19. Preparation of 4-chloro-3-(dimethylamino)-2-fluorophenylboronic acid

N-(3-Bromo-6-chloro-2-fluorophenyl)-N,N-dimethylaniline (0.88 g 3.5 mmol) was dissolved in ether (10 mL) and cooled to −60° C. under nitrogen. n-Butyl lithium (0.23 g, 3.6 mmol, 1.45 mL of a 2.5M solution) was added dropwise via syringe keeping the temperature under −55° C. After 0.5 hours, trimethylborate (0.40 g, 0.38 mmol) was added via syringe and the reaction was allowed to warm to room temperature. 1N HCl (3.5 mL) was added and the mixture was stirred for 0.5 hours. The mixture was diluted with water and extracted with ether. The organic phase was dried and concentrated to give 0.75 g of a foam that was triturated with hexanes. The resulting solid was collected by filtration and dried to give 4-chloro-3-(dimethylamino)-2-fluorophenylboronic acid (0.5 g, 2.3 mmol) as an off-white solid. $^1$H NMR (DMSO-$d_6$) revealed the solid to be a mixture of what appears to be the boronic acid and anhydrides. The solid was subsequently used without further purification or characterization.

20. Preparation of 2,6-dibromo-5-chloropyrimidine-4-carboxylic acid methyl ester Methyl 5-chloroorotate (33.8 g, 165 mmol, see H. Gershon, *J. Org. Chem.* 1962, 27, 3507-3510 for preparation) and phosphorous oxybromide (100 g, 349 mmol) were combined in sulfolane (200 mL). The resulting suspension was heated at 100-110° C. for 2 hours and then allowed to cool to room temperature. The cooled reaction mixture was poured onto ice and the product was extracted with hexane (4×150 mL). The organic extracts were combined and concentrated to yield 2,6-dibromo-5-chloropyrimidine-4-carboxylic acid methyl ester (32.0 g, 58.7% yield) that was used in subsequent reactions without further purification. An analytical sample was recrystallized from heptane: mp 92-93° C.

21. Preparation of 2-bromo-5-chloro-6-methylthiopyrimidine-4-carboxylic acid methyl ester An aqueous solution (15 mL) of sodium thiomethoxide (1.37 g, 19.5 mmol) was added dropwise to a solution of 2,6-dibromo-5-chloro-pyrimidine-4-carboxylic acid methyl ester (4.96 g, 15 mmol) in benzene (100 mL). The biphasic solution was stirred at room temperature for two hours at which point GC analysis indicated complete consumption of starting material. The organic phase was washed with brine twice, dried, and concentrated. Purification by column chromatography yielded 2-bromo-5-chloro-6-methylthiopyrimidine-4-carboxylic acid methyl ester (4.2 g, 94% yield): mp 105-106° C.

22. Preparation of 5-chloro-6-methylthio-2-trimethylstannanylpyrimidine-4-carboxylic acid methyl ester Hexamethylditin (5.0 g, 15.3 mmol), bis(triphenylphosphine)-palladium(II) dichloride (448 mg, 0.64 mmol), and 2-bromo-5-chloro-6-methylthiopyrimidine-4-carboxylic acid methyl ester (3.8 g, 12.75 mmol) were combined in dioxane and heated at 100° C. for 3 hours. The reaction mixture was then allowed to cool to room temperature, concentrated, and the product was isolated by column chromatography (Note: To avoid decomposition of product, column must be completed rapidly). This process yielded 5-chloro-6-methylthio-2-trimethylstannanylpyrimidine-4-carboxylic acid methyl ester as a clear oil product (2.0 g, 41% yield): $^1$H NMR (CDCl$_3$): δ 3.98 (s, 3 H), 2.58 (s, 3 H), 0.39 (s, 9 H).

23. Preparation of 6-amino-2,5-dichloropyrimidine-4-carboxylic acid methyl ester Ammonia was bubbled through a solution of 2,5,6-trichloro-pyrimidine-4-carboxylic acid methyl ester (15.94 g, 66 mmol, see H. Gershon, *J. Org. Chem.* 1962, 27, 3507-3510 for preparation) in p-dioxane (150 mL) for 30 minutes. The solvent was then removed and the residue partitioned between ethyl acetate and water. The organic phase was dried and concentrated under vacuum. The product was purified by column chromatography to provide 6-amino-2,5-dichloropyrimidine-4-carboxylic acid methyl ester (12.74 g, 87% yield): mp 164-166° C.

24. Preparation of 2-chloro-6-methylthiopyrimidine-4-carboxylic acid methyl ester An aqueous solution (45 mL) of sodium thiomethoxide (4.7 g, 67 mmol) was added dropwise to a solution of 2,6-dichloro-pyrimidine-4-carboxylic acid methyl ester (12.5 g, 60.4 mmol) in benzene (300 mL). The biphasic solution was stirred at room temperature for two hours at which point GC analysis indicated complete consumption of starting material. The organic phase was washed with brine twice, dried, and concentrated. Purification by column chromatography yielded 2-chloro-6-methylthiopyrimidine-4-carboxylic acid methyl ester (5.6 g, 42.6% yield): mp 90-92° C.; $^1$H NMR (CDCl$_3$): δ 7.78 (s, 1H), 4.00 (s, 3H), 2.63 (s, 3H).

25. Preparation of 2-chloro-6-methanesulfonylpyrimidine-4-carboxylic acid methyl ester 2-Chloro-6-methylthiopyrimidine-4-carboxylic acid methyl ester (4.38 g, 20 mmol) was dissolved in methylene chloride and m-chloroperoxy-benzoic acid (MCPBA; 70%) (12.3 g, 50 mmol) was added. The reaction mixture was stirred at room temperature for 3 days, concentrated under vacuum, and the residue partitioned between ethyl acetate and water. The organic phase was washed with a sodium bisulfite solution, washed with a sodium bicarbonate solution, dried, and concentrated under vacuum. The product was purified by column chromatography (methylene chloride/ethyl acetate gradient) to yield 2-chloro-6-methanesulfonylpyrimidine-4-carboxylic acid methyl ester (3.8 g, 76% yield): mp 127-129° C.: $^1$H NMR (CDCl$_3$): δ 8.56 (s, 1H), 4.09 (s, 3H), 3.34 (s, 3H).

26. Preparation of 6-amino-2-chloropyrimidine-4-carboxylic acid methyl ester 2-Chloro-6-methanesulfonylpyrimidine-4-carboxylic acid methyl ester (3.7 g, 14.75 mmol) was dissolved in dioxane and 7N ammonia in methanol was added. The reaction mixture was stirred at room temperature for 3 hours, concentrated under vacuum, and the residue partitioned between ethyl acetate and water. The organic phase was dried and concentrated. The product was purified by column chromatography to provide 6-amino-2-chloropyrimidine-4-carboxylic acid methyl ester (2.35 g, 85% yield): $^1$H NMR (DMSO-$d_6$): δ 7.6 (br s, 1H), 7.00 (s, 1H), 3.84 (s, 3H), 3.33 (s, 3H).

27. Preparation of 5-chloro-2-(4-chloro-3-ethoxy-2-fluorophenyl)-6-methane-sulfonylpyrimidine-4-carboxylic acid methyl ester 2-Bromo-5-chloro-6-methylthiopyrimidine-4-carboxylic acid methyl ester (2.98 g, 10 mmol), (4-chloro-3-ethoxy-2-fluorophenyl)-trimethylstannane (3.37 g, 10 mmol), and bis(triphenylphosphine)palladium(II) dichloride (351 mg, 0.5 mmol) were combined in 20 mL N-methylpyrrolidinone and heated at 110° C. for 3 hours. The reaction mixture was allowed to cool to room temperature and was then diluted with water. The water was decanted from the sticky residue and the residue was washed with additional water. The residue was purified by column chromatography (ethyl acetate/hexane gradient) and the intermediate product was combined with 2.5 eq of MCPBA in methylene chloride and stirred overnight. The excess MCPBA was quenched by the addition of a sodium bisulfite solution and the product was extracted with diethyl ether. The organic phase was washed with sodium bicarbonate solution, concentrated, and purified by column chromatography (ethyl acetate/hexane gradient). A second purification by column chromatography (methylene chloride only) yielded 5-chloro-2-(4-chloro-3-ethoxy-2-fluorophenyl)-6-methanesulfonylpyrimidine-4-carboxylic acid methyl ester (350 mg, 8.3% yield): mp 164-166° C.

28. Preparation of 6-amino-5-chloro-2-(4-chloro-3-ethoxy-2-fluorophenyl)-pyrimidine-4-carboxylic acid methyl ester (Compound 1)

5-Chloro-2-(4-chloro-3-ethoxy-2-fluorophenyl)-6-methane-sulfonylpyrimidine-4-carboxylic acid methyl ester (350 mg, 0.83 mmol) was dissolved in 10 mL p-dioxane and 7N ammonia in methanol (0.43 mL, 3 mmol) was added. The reaction mixture was stirred at room temperature for 3 hours and then concentrated. The residue was partitioned between ethyl acetate and water and the organic phase was dried and concentrated. The product was purified by column chromatography to yield 6-amino-5-chloro-2-(4-chloro-3-ethoxy-2-fluorophenyl)-pyrimidine-4-carboxylic acid methyl ester (160 mg, 54% yield): $^1$H NMR (CDCl$_3$): δ 7.65 (dd, 1H), 7.24 (dd, 1H), 5.67 (br s, 2H), 4.22 (q, 2H), 4.03 (s, 3H), 1.46 (t, 3H).

29. Preparation of 5-chloro-2-(4-chloro-2,6-difluoro-3-methoxyphenyl)-6-methylthiopyrimidine-4-carboxylic acid methyl ester 5-Chloro-6-methylthio-2-trimethylstannanylpyrimidine-4-carboxylic acid methyl ester (500 mg, 1.3 mmol), 1-chloro-3,5-difluoro-4-iodo-2-methoxybenzene (475 mg, 1.6 mmol) and Pd[P(o-Tol)$_3$]Cl$_2$ (100 mg, 0.13 mmol) were combined in 3 mL deaerated 1,2-dichloroethane. The resulting solution was heated at 130° C. for 20 minutes in a CEM Discover microwave. This process was repeated with another 500 mg sample of the stannane. The solvent was removed from the combined reaction mixtures and the residue was chromatographed on a 50 mm×250 mm YMC AQ column using 75% acetonitrile-25% 0.1% v/v H$_3$PO$_4$ to yield 5-chloro-2-(4-chloro-2,6-difluoro-3-methoxyphenyl)-6-methylthio-pyrimidine-4-carboxylic acid methyl ester (153 mg, 15% yield): mp 144-146° C.; MS: m/z=394.

30. Preparation of 6-amino-5-chloro-2-(4-chloro-2,6-difluoro-3-methoxy-phenyl)pyrimidine-4-carboxylic acid methyl ester (Compound 2)

5-chloro-2-(4-chloro-2,6-difluoro-3-methoxyphenyl)-6-methylthiopyrimidine-4-carboxylic acid methyl ester (150 mg, 0.38 mmol) was dissolved in 10 mL methylene chloride and treated with 70% MCPBA (240 mg, 0.95 mmol). After stirring for 2 hours an additional 100 mg of MCPBA was added and stirring was continued for 18 hours. The mixture was stirred with 5 mL 10% NaHSO$_3$ solution for 20 minutes. The separated organic phase was washed with 10% NaHCO$_3$ solution (5 mL), washed with water (5 mL), dried, and concentrated. The residue was dissolved in 10 mL 0.5M ammonia in dioxane and stirred at 25° C. for 20 hours and then concentrated under vacuum. The residue was taken up in 10 mL ethyl acetate, washed with 10 mL of water, washed with 5 mL of brine, dried, and concentrated to give 6-amino-5-chloro-2-(4-chloro-2,6-difluoro-3-methoxyphenyl)pyrimidine-4-carboxylic acid methyl ester (51 mg, 37% yield): $^1$H NMR (CDCl$_3$): δ 7.03 (dd, 1H), 5.87 (br s, 2H), 4.0 (s, 3H), 3.93 (d, 3H).

31. Preparation of 6-amino-5-chloro-2-(4-chloro-2-fluoro-3-methoxyphenyl)-pyrimidine-4-carboxylic acid methyl ester (Compound 3)

6-Amino-2,5-dichloropyrimidine-4-carboxylic acid methyl ester (888 mg, 4 mmol), 2-(4-chloro-2-fluoro-3-methoxyphenyl)-[1,3,2]-dioxaborinane (1.47 g, 6 mmol), bis(triphenylphosphine)palladium(II) dichloride (280 mg, 0.4 mmol), and cesium fluoride (1.21 g, 8 mmol) were combined in 8 mL of 1,2-dimethoxyethane and 8 mL of water. The reaction mixture was heated at 80° C. for 3 hours and the cooled reaction mixture was partitioned between ethyl acetate and water. The organic phase was washed with water, dried, and concentrated. The product was purified by column chromatography (ethyl acetate/hexane gradient) then purified again by column chromatography (methylene chloride/ethyl acetate gradient) to yield 6-amino-5-chloro-2-(4-chloro-2-fluoro-3-methoxyphenyl)pyrimidine-4-carboxylic acid methyl ester (738 mg, 53.5% yield): $^1$H NMR (CDCl$_3$): δ 7.64 (dd, 1H), 7.22 (dd, 1H), 5.64 (br s, 2H), 4.01 (s, 3H), 3.99 (d, 3H).

The following compounds were prepared according to the procedure of Example 31 utilizing either boronic acid esters or boronic acids:

6-Amino-5-chloro-2-(4-chloro-2-fluoro-3-methylthiophenyl)pyrimidine-4-carboxylic acid methyl ester (Compound 4): $^1$H NMR (CDCl$_3$): δ 7.83 (dd, 1H), 7.33 (dd, 1H), 5.71 (br s, 2H), 4.01 (s, 3H), 2.5 (d, 3H). 6-Amino-5-chloro-2-(4-chloro-2-fluoro-5-methoxyphenyl)pyrimidine-4-carboxylic acid methyl ester (Compound 5): $^1$H NMR (CDCl$_3$): δ 7.53 (d, 1H), 7.22 (d, 1H), 5.71 (br s, 2H), 4.02 (s, 3H), 3.95 (s, 3H). 6-Amino-5-chloro-2-(2,4-dichloro-3-methoxyphenyl)pyrimidine-4-carboxylic acid methyl ester (Compound 6): $^1$H NMR (CDCl$_3$): δ 7.39 (m, 2H), 5.71 (br s, 2H), 4.02 (s, 3H), 3.95 (s, 3H). 6-Amino-5-chloro-2-(4-chloro-3-difluoromethyl-2-fluorophenyl)pyrimidine-4-carboxylic acid methyl ester (Compound 7): mp 155-157° C. 6-Amino-5-chloro-2-(4-chloro-3-dimethylamino-2-fluorophenyl)pyrimidine-4-carboxylic acid methyl ester (Compound 8): mp 143-144° C. 6-Amino-5-chloro-2-(4-fluorobenzo[1,3]dioxol-5-yl)pyrimidine-4-carboxylic acid methyl ester (Compound 9): $^1$H NMR (CDCl$_3$): δ 7.59 (dd, 1H), 6.72 (dd, 1H), 6.08 (s, 2H), 5.6 (br s, 2H), 4.03 (s, 3H). 6-Amino-5-chloro-2-[4-chloro-3-(2,2-difluoroethoxy)-2-fluorophenyl]-pyrimidine-4-carboxylic acid methyl ester (Compound 10): mp 139-141° C. 6-Amino-5-chloro-2-(4-chloro-2-fluoro-3-methylphenyl)pyrimidine-4-carboxylic acid methyl ester (Compound 11): mp 166-168° C.

32. Preparation of 6-amino-2-(4-chloro-2-fluoro-3-methoxy-phenyl)-pyrimidine-4-carboxylic acid methyl ester.

6-Amino-2-chloro-pyrimidine-4-carboxylic acid methyl ester (2.25 g, 12 mmol), 4-chloro-2-fluoro-3-methoxyphenylboronic acid (3.27 g, 16 mmol), and bis(triphenylphosphine)palladium(II) dichoride (842 mg, 1.2 mmol) were combined in 12 mL of dimethoxyethane and 12 mL of water. The reaction mixture was heated at 80° C. for 2 hours and the cooled reaction mixture was partitioned between ethyl acetate and water. The organic phase was washed with water, dried, and concentrated under vacuum. The product was purified by column chromatography to yield 6-amino-2-(4-chloro-2-fluoro-3-methoxy-phenyl)pyrimidine-4-carboxylic acid methyl ester (2.0 g, 53.5% yield): mp 188-190° C.: $^1$H NMR (CDCl$_3$): δ 7.66 (dd, 1H), 7.22 (dd, 1H), 7.14 (s, 1H), 5.25 (br s, 2H), 4.0 (s, 3H), 3.99 (s, 3H).

33. Preparation of 6-amino-2-(4-chloro-2-fluoro-3-methoxy-phenyl)-5-fluoro-pyrimidine-4-carboxylic acid methyl ester (Compound 12).

6-Amino-2-(4-chloro-2-fluoro-3-methoxy-phenyl)-pyrimidine-4-carboxylic acid methyl ester (778 mg, 2.5 mmol) and F-TEDA (974 mg, 2.75 mmol) were combined in acetonitrile and heated at reflux for 4 hours (reaction made little progress after 1 hour). The reaction mixture was cooled to room temperature and filtered. The filtrate was concentrated, purified by column chromatography, and then purified a second time by preparative HPLC to yield 6-amino-2-(4-chloro-2-fluoro-3-methoxyphenyl)-5-fluoropyrimidine-4-carboxylic acid methyl ester (26 mg, 3.2% yield): mp 200-202° C.: $^1$H NMR (CDCl$_3$): δ 7.62 (dd, 1H), 7.21 (dd, 1H), 5.40 (br s, 2H), 4.02 (s, 3H), 4.0 (d, 3H)

34. Preparation of 6-amino-5-bromo-2-(4-chloro-2-fluoro-3-methoxyphenyl)-pyrimidine-4-carboxylic acid methyl ester (Compound 13)

6-Amino-2-(4-chloro-2-fluoro-3-methoxy-phenyl)-pyrimidine-4-carboxylic acid methyl ester (778 mg, 2.5 mmol) and N-bromosuccinimide (489 mg, 2.75 mmol) were combined in chloroform and heated at reflux for 12 hours. The cooled reaction mixture was concentrated and the product was isolated by column chromatography to yield 6-amino-5-bromo-2-(4-chloro-2-fluoro-3-methoxyphenyl)pyrimidine-4-carboxylic acid methyl ester (752 mg, 77% yield): mp 173-175° C.: $^1$H NMR (CDCl$_3$): δ 7.66 (dd, 1H), 7.24 (dd, 1H), 5.73 (br s, 2H), 4.03 (s, 3H), 4.01 (d, 3H).

35. Preparation of 6-amino-5-chloro-2-(4-chloro-2-fluoro-3-methanesulfinyl-phenyl)pyrimidine-4-carboxylic acid methyl ester 6-Amino-5-chloro-2-(4-chloro-2-fluoro-3-methylthiophenyl)pyrimidine-4-carboxylic acid methyl ester (2.4 g, 6.63 mmol) was dissolved with heating in a minimum amount of trifluoroethanol (50 mL). After allowing the reaction mixture to cool to room temperature, 30% hydrogen peroxide (3.0 mL, 26.5 mmol) was added and the reaction mixture was stirred for 2 days. An aqueous solution of sodium sulfite (10% solution) was added to quench excess oxidant (exotherm noted) and the reaction mixture was stirred for 1 hour. Additional water was then added and the reaction mixture was filtered. The precipitate was found to be pure 6-amino-5-chloro-2-(4-chloro-2-fluoro-3-methanesulfinylphenyl)pyrimidine-4-carboxylic acid methyl ester (2.13 g, 85% yield): mp 256-258° C.: $^1$H NMR (CDCl$_3$): δ 8.03 (dd, 1H), 7.54 (dd, 1H), 3.92 (s, 3H), 3.13 (s, 3H).

36. Preparation of 6-amino-5-chloro-2-(4-chloro-2-fluoro-3-trifluoro-methylthiophenyl)pyrimidine-4-carboxylic acid methyl ester (Compound 14)

6-Amino-5-chloro-2-(4-chloro-2-fluoro-3-methanesulfinyl-phenyl)pyrimidine-4-carboxylic acid methyl ester (378 mg, 1 mmol) was suspended in trifluoroacetic anhydride (5 mL) and the reaction mixture was heated at 60° C. in a sealed tube for 3 hours. The reaction mixture was allowed to cool to room temperature and the excess trifluoroacetic anhydride was removed under reduced pressure. To the residue was added 40 mL of a 1:1 mixture of triethylamine and methanol that was cooled to 0° C. The reaction mixture was immediately concentrated under vacuum and the resulting product redissolved in acetonitrile. To this solution was added trifluoromethyliodide (1.96 g, 10 mmol) condensed with a cold finger. The reaction mixture was placed in a glass sealed reaction vessel and irradiated with UV light for 15 minutes. The reaction mixture was then concentrated under vacuum and the residue was stirred in methanol overnight to remove the amine protecting group. The reaction mixture was concentrated once more and purified by column chromatography to yield 6-amino-5-chloro-2-(4-chloro-2-fluoro-3-trifluoromethylthiophenyl)pyrimidine-4-carboxylic acid methyl ester (238 mg, 57% yield): mp 167-169° C.: $^1$H NMR (CDCl$_3$): δ 8.13 (dd, 1H), 7.47 (dd, 1H), 5.69 (br s, 2H), 4.02 (s, 3H).

37. Preparation of 6-amino-5-chloro-2-(4-chloro-2-fluoro-3-methoxyphenyl)-pyrimidine-4-carboxylic acid (Compound 15)

6-Amino-5-chloro-2-(4-chloro-2-fluoro-3-methoxyphenyl)-pyrimidine-4-carboxylic acid methyl ester (156 mg, 0.45 mmol) was dissolved in 15 mL methanol and 1 mL of 2N sodium hydroxide (2 mmol) was added. The reaction mixture was stirred at room temperature for 2 hours and then acidified with a slight excess of 2N HCl. The resulting solution was concentrated under a nitrogen stream and several crops of crystals were collected during this process yielding 6-amino-5-chloro-2-(4-chloro-2-fluoro-3-methoxyphenyl)-pyrimidine-4-carboxylic acid (100 mg, 66.7% yield): mp 172-173° C.: $^1$H NMR (DMSO-d$_6$): δ 8.0 (br, 1H), 7.63 (dd, 1H), 7.43 (dd, 1H), 3.92 (s, 3H).

Other compounds prepared by the method of Example 37 include:

6-Amino-5-chloro-2-(4-chloro-2-fluoro-3-methylthiophenyl)pyrimidine-4-carboxylic acid (Compound 16): mp 139-141° C. 6-Amino-5-chloro-2-(4-chloro-2-fluoro-5-methoxyphenyl)pyrimidine-4-carboxylic acid (Compound 17): mp 202-204° C. 6-Amino-5-chloro-2-(2,4-dichloro-3-methoxyphenyl)pyrimidine-4-carboxylic acid (Compound 18): 139-141° C. 6-Amino-5-chloro-2-(4-chloro-3-ethoxy-2-fluorophenyl)pyrimidine-4-carboxylic acid (Compound 19): mp 132-134° C. 6-Amino-5-chloro-2-(4-chloro-2-fluoro-3-methylphenyl)pyrimidine-4-carboxylic acid (Compound 20): mp 210-212° C. 6-Amino-5-chloro-2-[4-chloro-3-(2,2-difluoroethoxy)-2-fluorophenyl]-pyrimidine-4-carboxylic acid (Compound 21): $^1$H NMR (DMSO-d$_6$+ D$_2$O): δ 7.7 (dd, 1H), 7.46 (dd, 1H), 6.34 (tt, 1H), 4.41 (td, 2H). 6-Amino-5-chloro-2-(4-fluoro-benzo[1,3]dioxol-5-yl)

pyrimidine-4-carboxylic acid (Compound 22): $^1$H NMR (DMSO-d$_6$+D$_2$O): δ 7.48 (dd, 1H), 6.91 (d, 1H), 8.2 (s, 2H). 6-Amino-5-chloro-2-(4-chloro-3-dimethylamino-2-fluorophenyl)pyrimidine-4-carboxylic acid (Compound 23): mp 181-183° C. 6-Amino-5-chloro-2-(4-chloro-3-difluoromethyl-2-fluorophenyl)pyrimidine-4-carboxylic acid (Compound 24): mp 166-168° C. 6-Amino-5-bromo-2-(4-chloro-2-fluoro-3-methoxyphenyl)pyrimidine-4-carboxylic acid (Compound 25) mp 173-175° C.

38. Preparation of Herbicidal Compositions

In the following illustrative compositions, parts and percentages are by weight.

EMULSIFIABLE CONCENTRATES

| | WT % |
|---|---|
| Formulation A | |
| Compound 1 | 26.2 |
| Polyglycol 26-3 | 5.2 |
| Nonionic emulsifier-(di-sec-butyl)-phenyl-poly(oxypropylene)block polymer with (oxyethelene). The polyoxyethelene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |
| Formulation B | |
| Compound 3 | 3.5 |
| Sunspray 11N (paraffin oil) | 40.0 |
| Polyglycol 26-3 | 19.0 |
| Oleic acid | 1.0 |
| Xylene range aromatic solvent | 36.5 |
| Formulation C | |
| Compound 6 | 13.2 |
| Stepon C-65 | 25.7 |
| Ethomeen T/25 | 7.7 |
| Ethomeen T/15 | 18.0 |
| Xylene range aromatic solvent | 35.4 |
| Formulation D | |
| Compound 2 | 30.0 |
| Agrimer A1-10LC (emulsifier) | 3.0 |
| N-methyl-2-pyrrolidone | 67.0 |
| Formulation E | |
| Compound 4 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

WETTABLE POWDERS

| | WT % |
|---|---|
| Formulation F | |
| Compound 15 | 26.0 |
| Polyglycol 26-3 | 2.0 |
| Polyfon H | 4.0 |
| Zeosyl 100 (Precipitated hydrated SiO$_2$) | 17.0 |
| Barden clay + inerts | 51.0 |

WETTABLE POWDERS (continued)

| | WT % |
|---|---|
| Formulation G | |
| Compound 19 | 62.4 |
| Polyfon H (sodium salt of lignin sulfonate) | 6.0 |
| Sellogen HR (sodium naphthalene sulfonate) | 4.0 |
| Zeosyl 100 | 27.6 |
| Formulation H | |
| Compound 21 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

WATER DISPERSIBLE GRANULES

| | WT % |
|---|---|
| Formulation I | |
| Compound 25 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

GRANULES

| | WT % |
|---|---|
| Formulation J | |
| Compound 20 | 5.0 |
| Celetom MP-88 | 95.0 |

The active ingredient is applied in a polar solvent such as N-methylpyrrollidinone, cyclohexanone, gamma-butyrolactone, etc. to the Celetom MP 88 carrier or to other suitable carriers. The resulting granules can be applied by hand, granule applicator, airplane, etc. in order to control weeds.

| | WT % |
|---|---|
| Formulation K | |
| Compound 18 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

|  | WT % |
|---|---|
| Formulation L | |
| Compound 23 | 3.67 |
| Monoethanolamine pH buffer | 0.5 |
| Water | 95.83 |

The active ingredient is dissolved in an appropriate amount of water and the additional monoethanolamine is added as a buffer. A water-soluble surfactant may be added. Other aids may be incorporated to improve physical, chemical and/or formulation properties.

39. Evaluation of General Postemergence Herbicidal Activity

Seeds or nutlets of the desired test plant species were planted in Sun Gro MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v (volume/volume) mixture of acetone and dimethyl sulfoxide (DMSO) and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain 1/2X, 1/4X, 1/8X and 1/16X rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Table 1 and Table 2.

TABLE 1

Post-emergent Weed Control

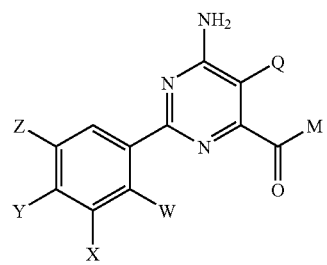

| | | | | | | | % Control | | |
|---|---|---|---|---|---|---|---|---|---|
| Compound # | M | Q | W | X | Y | Z | Rate (g ai/ha) | CHEAL | ABUTH | HELAN |
| 1 | OCH$_3$ | Cl | F | OCH$_2$CH$_3$ | Cl | H | 140 | 100 | 100 | 100 |
| 3 | OCH$_3$ | Cl | F | OCH$_3$ | Cl | H | 140 | 100 | 100 | 100 |
| 4 | OCH$_3$ | Cl | F | SCH$_3$ | Cl | H | 140 | 65 | 100 | 100 |
| 5 | OCH$_3$ | Cl | F | H | Cl | OCH$_3$ | 140 | 100 | 95 | 95 |

TABLE 1-continued

Post-emergent Weed Control

|  |  |  |  |  |  |  | % Control | | |
|---|---|---|---|---|---|---|---|---|---|
| Compound # | M | Q | W | X | Y | Z | Rate (g ai/ha) | CHEAL | ABUTH | HELAN |
| 6 | OCH$_3$ | Cl | Cl | OCH$_3$ | Cl | H | 140 | 100 | 95 | 100 |
| 7 | OCH$_3$ | Cl | F | CF$_2$H | Cl | H | 140 | 100 | 80 | 100 |
| 8 | OCH$_3$ | Cl | F | N(CH$_3$)$_2$ | Cl | H | 140 | 100 | 100 | 100 |
| 9 | OCH$_3$ | Cl | F | OCH$_2$O | | H | 140 | 90 | 95 | 100 |
| 10 | OCH$_3$ | Cl | F | OCH$_2$CF$_2$H | Cl | H | 140 | 85 | 75 | 80 |
| 11 | OCH$_3$ | Cl | F | CH$_3$ | Cl | H | 140 | 95 | 95 | 100 |
| 12 | OCH$_3$ | F | F | OCH$_3$ | Cl | H | 140 | 95 | 85 | 100 |
| 13 | OCH$_3$ | Br | F | OCH$_3$ | Cl | H | 140 | 100 | 100 | 100 |
| 14 | OCH$_3$ | Cl | F | SCF$_3$ | Cl | H | 140 | 50 | 80 | 90 |
| 15 | OH | Cl | F | OCH$_3$ | Cl | H | 140 | 100 | 100 | 100 |
| 16 | OH | Cl | F | SCH$_3$ | Cl | H | 140 | 15 | 85 | 100 |
| 17 | OH | Cl | F | H | Cl | OCH$_3$ | 140 | 100 | 50 | 80 |
| 18 | OH | Cl | Cl | OCH$_3$ | Cl | H | 140 | 100 | 75 | 95 |
| 19 | OH | Cl | F | OCH$_2$CH$_3$ | Cl | H | 140 | 90 | 95 | 95 |
| 20 | OH | Cl | F | CH$_3$ | Cl | H | 140 | 100 | 90 | 100 |
| 21 | OH | Cl | F | OCH$_2$CF$_2$H | Cl | H | 140 | 90 | 0 | 80 |
| 22 | OH | Cl | F | OCH$_2$O | | H | 140 | 95 | 80 | 90 |
| 23 | OH | Cl | F | N(CH$_3$)$_2$ | Cl | H | 140 | 100 | 95 | 95 |
| 24 | OH | Cl | F | CF$_2$H | Cl | H | 140 | 95 | 80 | 90 |
| 25 | OH | Br | F | OCH$_3$ | Cl | H | 140 | 100 | 95 | 100 |

CHEAL = lambsquarter (*Chenopodium album*)
ABUTH = velvetleaf (*Abutilon theophrasti*)
HELAN = sunflower (*Helianthus annuus*)

TABLE 2

Post-emergent Weed Control

|  |  |  |  |  |  |  | % Control | | |
|---|---|---|---|---|---|---|---|---|---|
| Compound # | M | Q | W | X | Y | Rate (g ai/ha) | CHEAL | ABUTH | HELAN |
| 2 | OCH$_3$ | Cl | F | OCH$_3$ | Cl | 140 | 100 | 90 | 100 |

CHEAL = lambsquarter (*Chenopodium album*)
ABUTH = velvetleaf (*Abutilon theophrasti*)
HELAN = sunflower (*Helianthus annuus*)

40. Evaluation of General Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 25 mL glass vial and was dissolved in 6 mL of a 97:3 v/v (volume/volume) mixture of acetone and DMSO to obtain concentrated stock solutions. If the test compound did not dissolve readily, the mixture was warmed and/or sonicated. The stock solutions obtained were diluted with 18 mL of a 0.1% v/v aqueous solution of Tween® 20 surfactant to obtain spray solutions containing the highest application rate. Additional application rates were obtained by serial dilution of 12 mL of the high rate solution into a solution containing 3 mL of 97:3 v/v mixture of acetone and DMSO and 9 mL of the 0.1% v/v aqueous solution of Tween® 20 surfactant to obtain 1/2X, 1/4X, 1/8X and 1/16X rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the soil surface. Control plants were sprayed in the same manner with the solvent blank.

The treated pots and control pots were placed in a greenhouse maintained with an approximate 15 hour photoperiod and temperatures of about. 23-29° C. during the day and 22-28° C. during the night. Nutrients and water were added on a regular basis and supplemental lighting was provided with overhead metal halide 1000-Watt lamps as necessary. The water was added by top-irrigation. After 20-22 days, the condition of the test plants that germinated and grew as compared with that of the untreated plants that emerged and grew was determined visually and scored on a scale of 0 to 100 percent where 0 corresponds to no injury and 100 corresponds to complete kill or no emergence.

Some of the compounds tested, application rates employed, plant species tested, and results are given in Table 3.

TABLE 3

| | Pre-emergent Weed Control | | | |
| --- | --- | --- | --- | --- |
| | | % Control | | |
| Compound # | Rate (g ai/ha) | CHEAL | ABUTH | HELAN |
| 2 | 140 | 90 | 100 | 20 |
| 6 | 140 | 100 | 60 | 90 |
| 7 | 140 | 70 | 75 | 90 |
| 10 | 280 | 60 | 80 | 0 |
| 11 | 140 | 60 | 100 | 100 |
| 15 | 140 | 100 | 100 | 100 |
| 16 | 140 | 50 | 80 | 80 |
| 17 | 140 | 95 | 100 | 0 |
| 18 | 140 | 100 | 100 | 100 |
| 19 | 280 | 75 | 80 | 90 |

CHEAL = lambsquarter (*Chenopodium album*)
ABUTH = velvetleaf (*Abutilon theophrasti*)
HELAN = sunflower (*Helianthus annuus*)

41. Evaluation of Postemergence Herbicidal Activity in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters. When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 25 mL glass vial and was dissolved in 8 mL of a 97:3 v/v mixture of acetone and DMSO to obtain concentrated stock solutions. If the test compound did not dissolve readily, the mixture was warmed and/or sonicated. The concentrated stock solutions obtained were diluted with 16 mL of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio to obtain spray solutions containing the highest application rates. Additional application rates were obtained by serial dilution of 12 mL of the high rate solution into a solution containing 4 mL of 97:3 v/v mixture of acetone and DMSO and 8 mL of an aqueous mixture containing acetone, water, isopropyl alcohol, DMSO, Agri-dex crop oil concentrate, and Triton X-77 surfactant in a 48.5:39.0:10.0:1.5:1.0:0.02 v/v ratio to obtain 1/2X, 1/4X, 1/8X and 1/16X rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above average plant canopy height. Control plants were sprayed in the same manner with the blank.

The treated plants and control plants were placed in a greenhouse as described above and watered by sub-irrigation to prevent wash-off of the test compounds. After 20-22 days, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Table 4.

TABLE 4

Post-emergent Control of Several Key Weeds in Wheat and Barley

| | | % Control | | | | | |
|---|---|---|---|---|---|---|---|
| Compound # | Rate (g ai/ha) | TRZAS | HORVS | GALAP | LAMPU | PAPRH | VERPE |
| 1 | 35 | 0 | 0 | 99 | 85 | 100 | 20 |
| 2 | 35 | 0 | 0 | 95 | 95 | 100 | 50 |
| 3 | 17.5 | 0 | 0 | 95 | 99 | 100 | 99 |
| 6 | 70 | 10 | 0 | 85 | 99 | 99 | 99 |
| 7 | 17.5 | 15 | 0 | 60 | 90 | 95 | 95 |
| 8 | 35 | 15 | 0 | 70 | 85 | 100 | 95 |
| 9 | 70 | 15 | 0 | 90 | 100 | 40 | 30 |
| 10 | 70 | 5 | 0 | 65 | 85 | 95 | 20 |
| 13 | 17.5 | 0 | 0 | 90 | 95 | 100 | 95 |

TRZAS = wheat (*Triticum aestivum*)
HORVS = barley (*Hordeum vulare*)
GALAP = *Galium aparine*
LAMPU = *Lamium purpureum*
PAPRH = *Papaver rhoeas*
VERPE = *Veronica persica*

42. Evaluation of Herbicidal Activity in Transplanted Paddy Rice

Weed seeds or nutlets of the desired test plant species were planted in puddled soil (mud) prepared by mixing a non-sterilized mineral soil (28 percent silt, 18 percent clay, and 54 percent sand, with a pH of about 7.3 to 7.8 and an organic matter content of about 1.0 percent) and water at a ratio of 100 kg of soil to 19 L of water. The prepared mud was dispensed in 250 mL aliquots into 480 mL non-perforated plastic pots with a surface area of 91.6 square centimeters leaving a headspace of 3 centimeters in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 650 mL of mud contained in 960 mL non-perforated plastic pots with a surface area of 91.6 square centimeters 4 days prior to herbicide application. The paddy was created by filling the 3 centimeter headspace of the pots with water. When required to ensure good germination and healthy plants, a fungicide treatment and/or other chemical or physical treatment was applied. The plants were grown for 4-14 days in a greenhouse with an approximate 14 hour photoperiod which was maintained at about 29° C. during the day and 26° C. during the night. Nutrients were added as Osmocote (17:6:10, N:P:K+minor nutrients) at 2 g (grams) per cup. Water was added on a regular basis to maintain the paddy flood, and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 120 mL glass vial and was dissolved in 20 mL of acetone to obtain concentrated stock solutions. If the test compound did not dissolve readily, the mixture was warmed and/or sonicated. The concentrated stock solutions obtained were diluted with 20 mL of an aqueous mixture containing 0.01% Tween 20 (v/v). Application rates of 1/2X, 1/4X, 1/8X and 1/16X of the high rate were obtained by injecting an appropriate amount of the stock solution into the aqueous layer of the paddy. Control plants were treated in the same manner with the solvent blank.

The treated plants and control plants were placed in a greenhouse as described above and water was added as needed to maintain a paddy flood. After 20-22 days, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Table 5.

TABLE 5

Water-injected Control of Several Key Weeds in Rice

| | | % Control | | | |
|---|---|---|---|---|---|
| Compound # | Rate (g ai/ha) | ORYSA | SCPJU | CYPDI | MOOVA |
| 1 | 17.5 | 5 | 50 | 95 | 100 |
| 2 | 70 | 0 | 20 | 75 | 100 |
| 3 | 17.5 | 0 | 80 | 99 | 100 |
| 6 | 17.5 | 0 | — | 90 | 100 |
| 7 | 140 | 0 | 90 | 100 | 100 |
| 8 | 35 | 0 | 10 | 95 | 100 |
| 9 | 35 | 0 | 70 | 100 | 99 |
| 10 | 140 | 0 | 40 | 95 | 100 |
| 13 | 70 | 0 | 60 | 85 | 100 |

ORYSA = rice (*Orysa sativa* var. *Japonica*)
SCPJU = *Scirpus juncoides*
CYPDI = *Cyperus difformis*
MOOVA = *Monochoria vaginalis*

What is claimed is:

1. A compound of the formula I

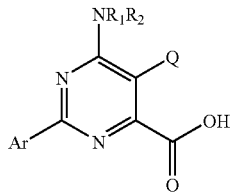

wherein

Q represents a halogen;

$R_1$ and $R_2$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated ring; and Ar represents a polysubstituted aryl group selected from the group consisting of a)

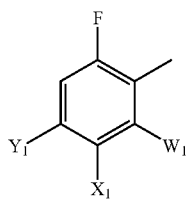

wherein $W_1$ represents F or Cl;

$X_1$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_1$ represents halogen or $C_1$-$C_4$ haloalkyl or, when $X_1$ and $Y_1$ are taken together, represents —O(CH$_2$)$_n$O— wherein n=1 or 2; and $R_3$ and R4 independently represent H or $C_1$-$C_4$ alkyl;

b)

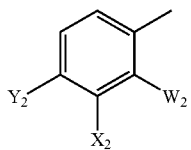

wherein $W_2$ represents F or Cl;

$X_2$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_2$ represents halogen or $C_1$-$C_4$ haloalkyl or, when $X_2$ and $Y_2$ are taken together, represents —O(CH$_2$)$_n$O— wherein n=1 or 2; and $R_3$ and $R_4$ independently represent H or $C_1$-$C_4$ alkyl; and c)

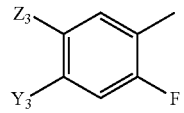

wherein $Y_3$ represents halogen or $C_1$-$C_4$ haloalkyl or, when $Y_3$ and $Z_3$ are taken together, represents —O(CH$_2$)$_n$O— wherein n=1 or 2;

$Z_3$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$; and $R_3$ and $R_4$ independently represent H or $C_1$-$C_4$ alkyl; and agriculturally acceptable derivatives of the carboxylic acid group.

2. A compound of claim 1 in which $R_1$ and $R_2$ independently represent H or $C_1$-$C_6$ alkyl.

3. A compound of claim 1 in which Q represents Cl or Br.

4. A compound of claim 1 in which Ar represents

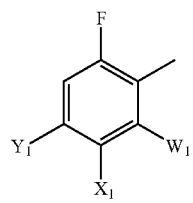

wherein $W_1$ represents F or Cl;

$X_1$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_1$ represents halogen or $C_1$-$C_4$ haloalkyl or, when $X_1$ and $Y_1$ are taken together, represents —O(CH$_2$)$_n$O— wherein n=1 or 2; and $R_3$ and $R_4$ independently represent H or $C_1$-$C_4$ alkyl.

5. A compound of claim 4 in which $X_1$ represents $C_1$-$C_4$ alkoxy or —$NR_3R_4$.

6. A compound of claim 4 in which $Y_1$ represents Cl.

7. A compound of claim 1 in which Ar represents

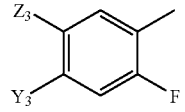

wherein $W_2$ represents F or Cl;

$X_2$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —$NR_3R_4$;

$Y_2$ represents halogen or $C_1$-$C_4$ haloalkyl or, when $X_2$ and $Y_2$ are taken together, represents —O(CH$_2$)$_n$O— wherein n=1 or 2; and $R_3$ and $R_4$ independently represent H or $C_1$-$C_4$ alkyl.

8. A compound of claim 7 in which $X_2$ represents $C_1$-$C_4$ alkoxy or —$NR_3R_4$.

9. A compound of claim 7 in which $Y_2$ represents Cl.

10. A compound of claim 1 in which Ar represents

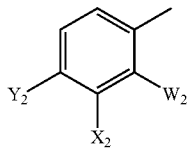

wherein
  $Y_3$ represents halogen, $C_1$-$C_4$ haloalkyl or, when $Y_3$ and $Z_3$ are taken together, represents —O(CH$_2$)$_n$O— wherein n=1 or 2;
  $Z_3$ represents $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio or —NR$_3$R$_4$.

11. A compound of claim 10 in which $Z_3$ represents $C_1$-$C_4$ alkoxy.

12. A compound of claim 10 in which $Y_3$ represents Cl.

13. A herbicidal composition comprising a herbicidally effective amount of a compound of Formula I, according to claim 1, in a mixture with an agriculturally acceptable adjuvant or carrier.

14. A method of controlling undesirable vegetation which comprises contacting the vegetation or the locus thereof with or applying to the soil to prevent the emergence of vegetation an herbicidally effective amount of a compound of Formula I, according to claim 1.

* * * * *